United States Patent [19]

Oebser et al.

[11] 4,285,336
[45] Aug. 25, 1981

[54] SCOLIOSIS ORTHOTIC SYSTEM

[75] Inventors: Alfred L. Oebser, Orange; David L. Porter, Sunset Beach, both of Calif.

[73] Assignee: Orthomedics, Inc., Brea, Calif.

[21] Appl. No.: 87,541

[22] Filed: Oct. 23, 1979

[51] Int. Cl.³ .............................................. A61F 5/02
[52] U.S. Cl. ...................................... 128/78; 128/75
[58] Field of Search .................. 128/75, 78, 83, 84 R, 128/84 C, 68, 69, 87 B, 89 R, DIG. 19

[56] References Cited

U.S. PATENT DOCUMENTS

| 6,023 | 1/1849 | Mellish | 128/78 |
|---|---|---|---|
| 507,172 | 10/1893 | Shelden | 128/78 |
| 709,055 | 9/1902 | Sheldon | 128/78 |
| 954,005 | 4/1910 | Roth | 128/78 |
| 1,562,935 | 11/1925 | Whisner | 128/78 |
| 2,181,689 | 11/1939 | Bell | 128/78 |
| 2,453,370 | 11/1948 | Hittenberger | 128/78 |
| 2,808,050 | 10/1957 | Ward | 128/78 |
| 3,095,875 | 7/1963 | Davidson et al. | 128/78 |
| 3,220,407 | 11/1965 | Connelly | 128/78 |
| 3,680,548 | 8/1972 | Brown | 128/69 |
| 3,696,439 | 10/1972 | Durham | 128/90 |
| 3,871,367 | 3/1975 | Miller | 128/78 |
| 3,926,183 | 12/1975 | Spiro | 128/78 |
| 3,945,376 | 3/1976 | Kuehnegger | 128/78 |
| 4,080,962 | 3/1978 | Berkeley | 128/78 |

OTHER PUBLICATIONS

*Orthopaedic Appliances Atlas;* vol. I, pp. 210–221, 228–235, published 1952 by J. W. Edwards, Ann Arbor, Mich.
*Fillauer Orthopedic Catalog;* P.O. Box 1678, Chattanouga, Tenn., pp. 61–69.
*Pope Brace Co. Catalog;* Kankakee, Illinois, pp. 21, 22.
Hall, J.; A Refined Concept in Orthotic Management of Scoliosis, in Orthotics & Prosthetics 12/75, vol. 29, No. 4, pp. 7–13.
*Spinal Orthotics;* Author-Unknown, 1977, pp. 37–42.

*Primary Examiner*—Robert W. Michell
*Assistant Examiner*—Arthur S. Rose

[57] ABSTRACT

An orthopedic brace for treatment of idiopathic scoliosis or curvature of the spine. A brace with an anterior panel and spaced right and left posterior panels, with substantially rigid iliac crest members at each side joining the anterior panel to the respective posterior panels. Adjustable straps are provided for interconnecting the spaced posterior panels, and a flexible pelvic band is carried at the lower ends of the panels for positioning about the pelvis of the wearer. The various additional components may be added to the basic lumbar brace as desired, including a thoracic sling, an anterior sternal upright, a chest band, and a neck band.

8 Claims, 12 Drawing Figures

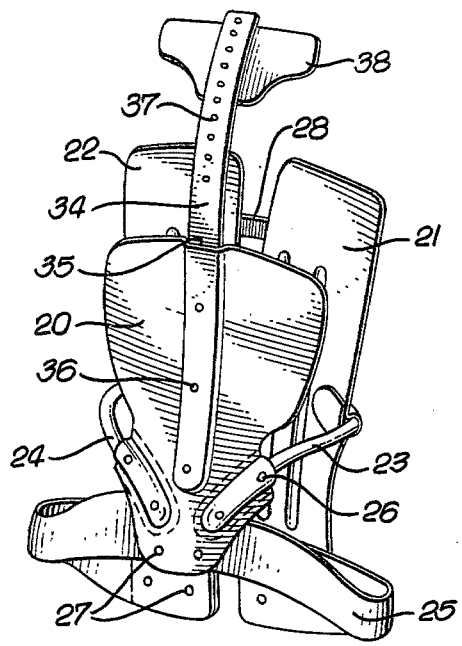
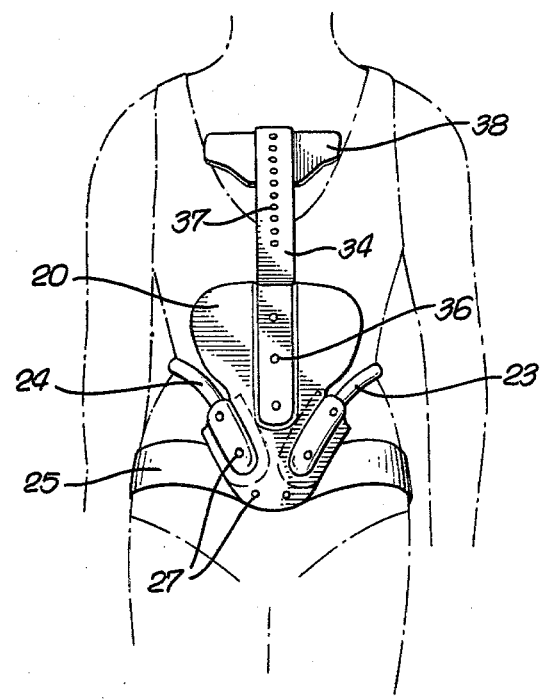
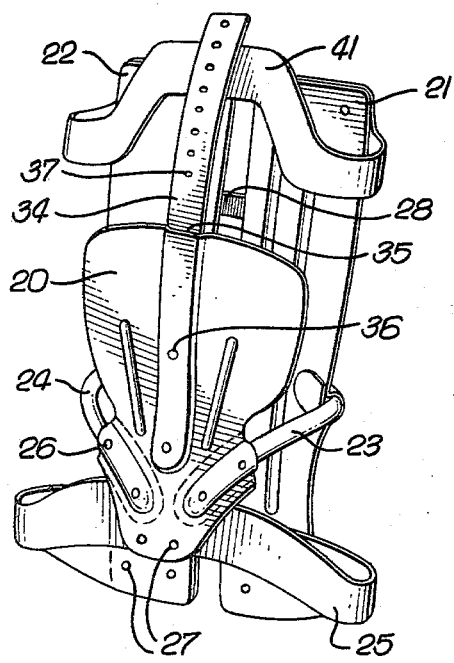
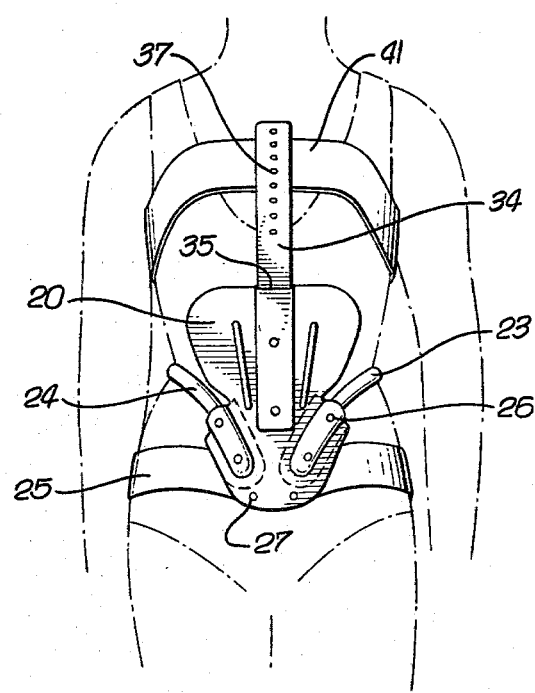

SCOLIOSIS ORTHOTIC SYSTEM

BACKGROUND OF THE INVENTION

This invention relates to orthopedic braces, sometimes referred to as scoliosis orthotic systems, for the non-operative treatment of idopathic scoliosis or curvature of the spine.

A wide variety of structures have been used in the past for this purpose. One sometimes referred to as the Milwaukee system, utilizes a girdle or corset fitted to the wearers body and positioned around the pelvis and chest, with appropriate attachments for the neck. Another structure is sometimes referred to as the Boston system, and utilizes a prefabricated girdle to which the super structure may be attached. Another prior art structure is shown in U.S. Pat. No.3,945,376. This unit utilizes various bars and straps joined by a rigid pelvic band positioned about the hips of the wearer, and flexible iliac crest members on each side at the crest or top of the pelvic structure.

These prior art devices have various disadvantages and it is an object of the present invention to provide a new and improved orthopedic brace which overcomes some of the undesirable features of the prior devices.

The molded girdle or corset is difficult to fit, often has to be custom made for a particular patient, and is relatively uncomfortable. Also, as the patient grows and the pelvis area becomes larger, the girdle tends to move upward on the patient and apply pressure on the lower ribs.

Another disadvantage of the prior art devices resides in the increased size and bulk of the wearer and hence the adverse cosmetic and psychological effects. Braces with a pelvic girdle or a rigid pelvic band providing mechanical support inherently make the wearer larger. It is an object of the present invention to provide a brace which eliminates the need for any rigid pelvic enclosing structure, thereby permitting the wearer to wear clothes of normal size. Also, while the conventional superstructures for chest and neck may be utilized with the brace of the present invention, these superstructures are not always essential and often may be omitted thereby reducing patient discomfort and improving the patient's appearance.

A further object of the present invention is to provide a brace which is assembled of stock components that are readily fitted to an individual patient without requiring body casts or special order parts or the like.

Other objects, advantages, features and results will more fully appear in the course of the following description.

SUMMARY OF THE INVENTION

The orthopedic brace of the present invention includes an anterior panel and spaced posterior panels joined at each side by substantially rigid iliac crest members. The right and left posterior panels are interconnected by adjustable straps fitting the brace to the patient. Also, the three panels are joined by a flexible pelvic band carried at the lower ends of the panels. The various components of the brace may be stocked components which are fitted together at the time the brace is fitted on the patient. Additional structures such as a thoracic sling, an anterior sternal upright, a chest band, and/or a Milwaukee type neck brace may be added as desired.

BRIEF DESCRIPTION OF THE DRAWINGS

FIG. 5 is a view similar to that of FIG. 1 showing a brace with an anterior sternal upright;

FIG. 6 is a front view of a patient wearing the brace of FIG. 5;

FIG. 7 is a view similar to that of FIGS. 1 and 5 showing a brace with a thoracic or chest band;

FIG. 8 is a front view of a patient wearing the brace of FIG. 7;

DESCRIPTION OF THE PREFERRED EMBODIMENTS

Figure 2:
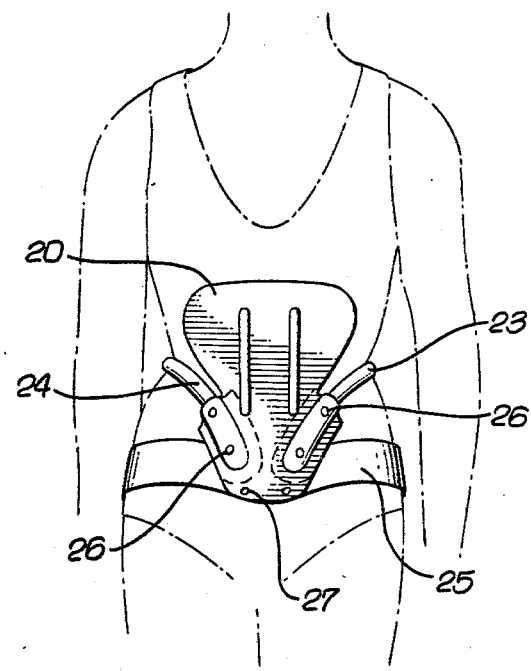
FIG. 2 is a front view of a patient wearing the brace of FIG. 1.
Figure 3:
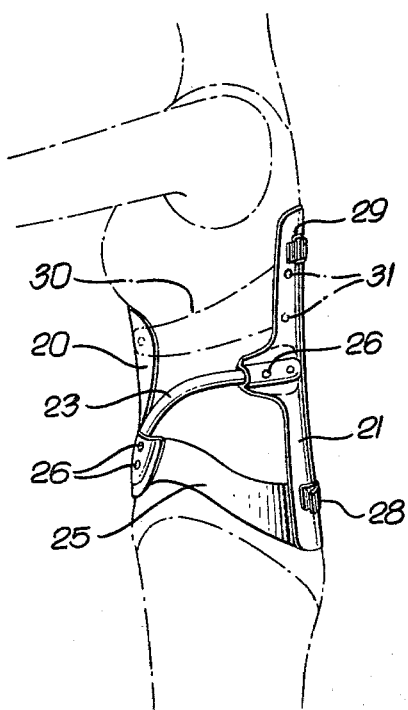
FIG. 3 is a side view of the patient of FIG. 2, showing a thoracic sling in phantom lines.
Figure 4:
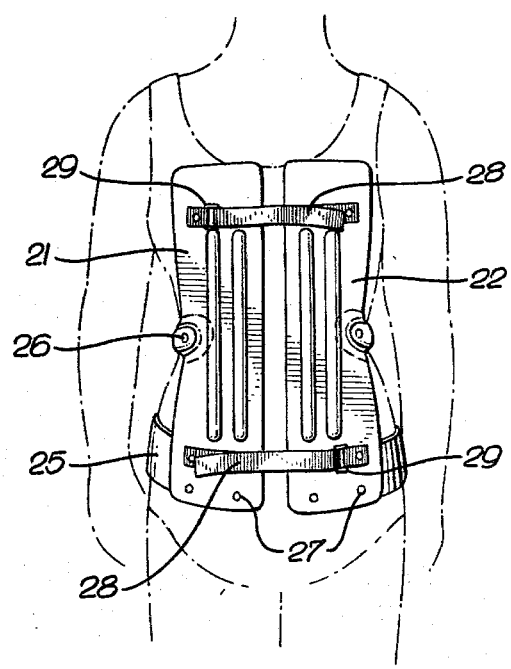
FIG. 4 is a back view of the patient of FIG. 2.

The brace as shown in FIGS. 1–4 includes an anterior panel 20, posterior panels 21, 22, iliac crest members 23, 24, and a pelvic band 25. The panels 20–22 preferably are made of a molded plastic with reinforcing ribs as illustrated, but could be made of metal or other stiff material if desired. The iliac crest members 23, 24 typically are made of plastic rod or tube and are joined at their ends to the panels, typically by having the ends of the rods enter molded sockets in the panels, with the rods retained by rivets or screws 26. The pelvic band 25 typically is a flexible plastic strip attached at its center to the lower end of the anterior panel 20 and attached at its ends to the lower ends of the posterior panels 21, 22 by rivets 27. The posterior panels 21, 22 are joined by straps 28 and buckles 29 attached to the respective panels, as best seen in FIG. 4.

The iliac crest members 23, 24 are substantially rigid as compared to the flexible pelvic band 25 and to the rubber hose used for iliac crest members in the aforesaid U.S. Pat. No. 3,945,376. These crest members serve to maintain the positional relationship between the panels and help to maintain the brace in position on the wearer. These crest members fit along the iliac crest or upper edge of the pelvic structure of the wearer, as seen in FIGS. 2 and 3.

Figure 1:
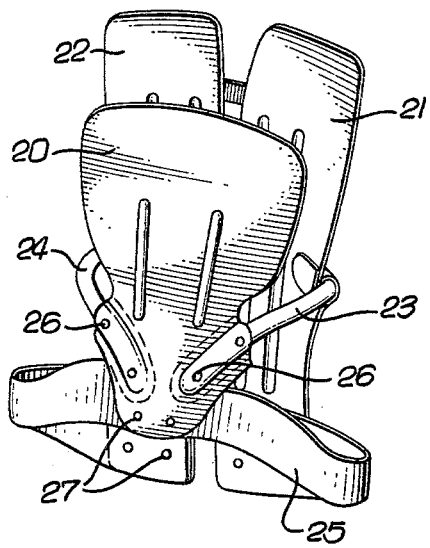
FIG. 1 is a perspective view from the front of an orthopedic brace incorporating the presently preferred embodiment of the invention.

The panels and crest members may be stock pieces of standard size. The patient's waist is measured and a brace assembly comprising the three panels and the two crest members with appropriate size crest members is selected and placed on the patient and the straps 28 are fastened into buckles 29, drawing the brace tight. Then the upper edge of the anterior panel and the upper and lower edges of the posterior panels may be trimmed to the appropriate size. The pelvic band is initially attached only to the anterior panel. After the panels have been trimmed, the pelvic band is wrapped around the pelvis in position to blend with the contour of the pelvis and the ends of the pelvic band and the lower half of the posterior panels are marked and drilled and the components are joined together producing the finished structure as shown in FIG. 1 ready for wearing by the patient.

With this brace configuration, the iliac crest members are the main stabilizing factor, typically being formed of ¾" thick plastic rod, such as polypropylene, providing a substantially rigid joinder between the anterior and posterior panels. The flexible pelvic band is of one piece and fits snugly around the pelvis maintaining the lower ends of the panels in position. The posterior panels are joined together in the back only by the straps 28. The iliac crest members 23 and 24 and/or pelvic band 25 can be adjusted for patient growth so that the desired vertical positioning of the brace can be maintained as the patient grows.

Various additional components may be incorporated in the brace as desired. One such attachment is a thoracic sling, as shown in phantom lines in FIG. 3. A flexible strap 30 is affixed to the underside of the posterior panel 21, as by rivets 31. The strap 30 extends around laterally to the anterior panel 20 and may be permanently attached by a rivet or adjustably attached by a plurality of openings in the strap and a stud in the panel.

A modification of the brace with an anterior sternal upright is shown in FIGS. 5 and 6, where components corresponding to those of FIGS. 1-4 are identified by the same reference numerals. A bar 34, typically of aluminum, is shaped to have a contour symmetrical to that of the body. The lower end of the bar 34 is attached to the anterior panel 20, preferably by positioning in a groove 35 and attachment by rivets or screws at 36. A plurality of openings 37 is provided in the upper end of the bar 35 for attachment of a pressure pad 38. During fitting, the bar 34 may be bent to obtain the desired contour, and the pad may be mounted on the bar at the desired elevation. The pad may be moved upwardly or downwardly on the bar as the patient grows and or otherwise changes.

Figure 9:
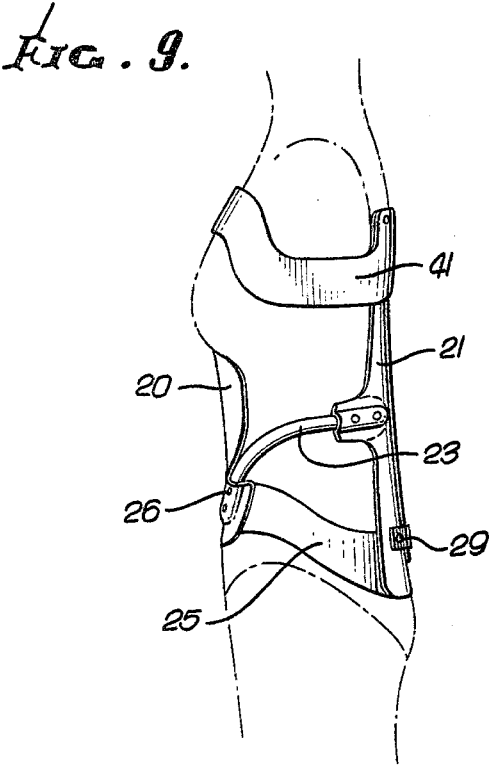
FIG. 9 is side view of a patient wearing the brace of FIG. 7.
Figure 10:
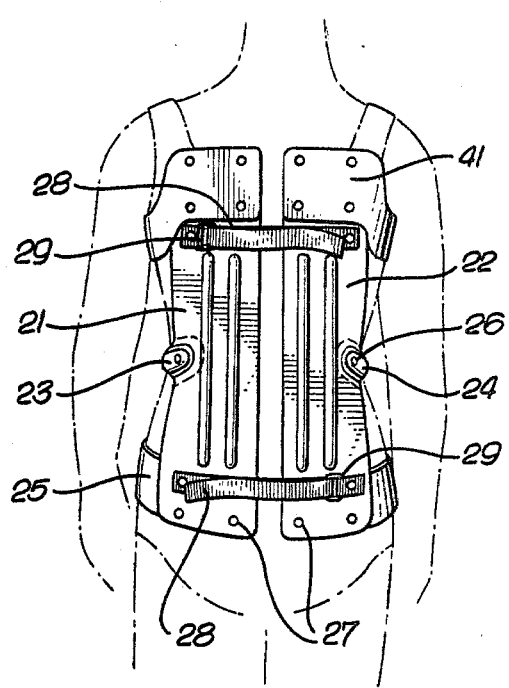
FIG. 10 is a back view of a patient wearing the brace of FIG. 7.

Another configuration is illustrated in FIGS. 7-10 where components corresponding to those occurring in earlier figures are identified by the same reference numerals. A band 41 is centrally attached to the bar 34 as by screws or rivets, and the respective ends of the band 41 are attached to the upper ends of the posterior panels 21, 22 with similar screws or rivets. The band 41 is shaped to fit under the arms, as seen in FIGS. 7 and 9 and usually is formed of a relatively stiff material. This configuration may be utilized for thoracic orthosis and for post fusion orthosis, with the particular shape and position of the band being chosen for the specific desired use.

Figure 11:
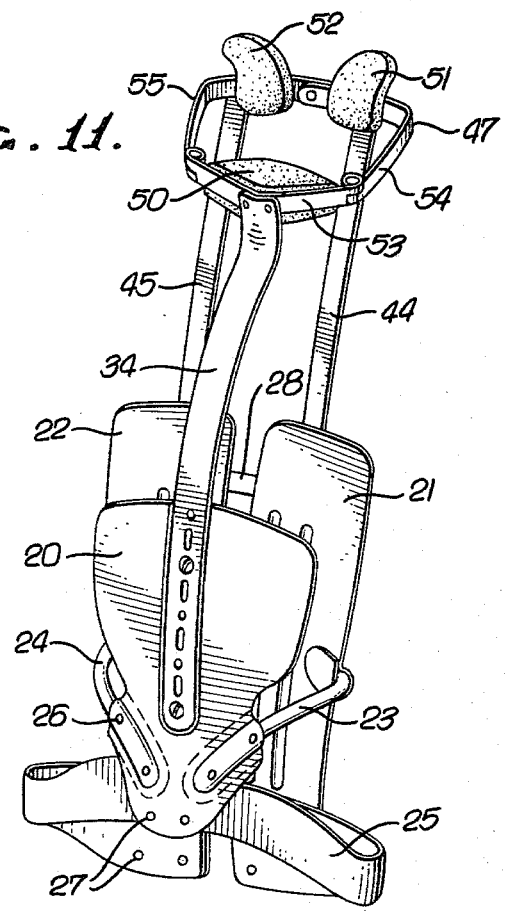
FIG. 11 is a view similar to that of FIGS. 1, 5 and 7 showing a brace with a Milwaukee type neck ring.
Figure 12:
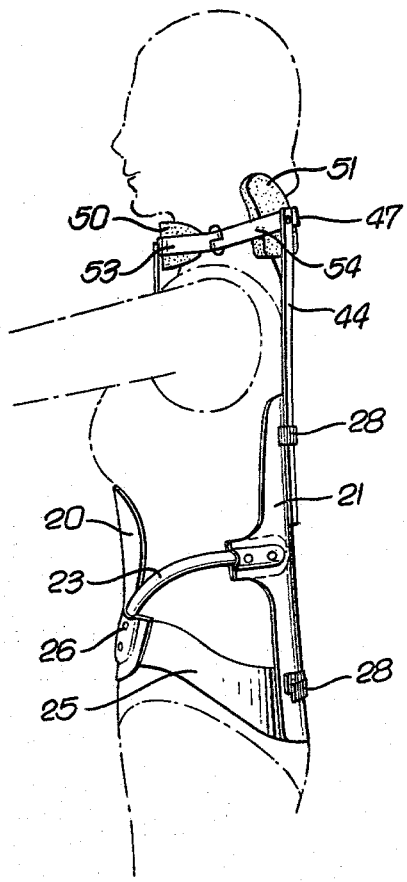
FIG. 12 is a side view of patient wearing the brace of FIG. 11.

Another alternative configuration with superstructure or neck band is shown in FIGS. 11 and 12, where elements corresponding to those shown in earlier figures are identified by the same reference numerals. Vertically extending bars 44, 45 are attached to the posterior panels 21, 22, respectively. A ring or neck band 47 is carried at the upper ends of the bars 34, 44, 45, with pads 50, 51, 52 mounted on the ring 47. The ring 47 typically is formed of three pieces 53, 54, 55, with piece 53 carried on the bar 34, piece 54 hinged to piece 53 and attached to bar 44, and piece 55 hinged to piece 53 and attached to bar 45, with the pieces 54, 55 joined by a screw or rivet or otherwise as desired.

The medical uses of the orthopedic brace of the present invention is substantially the same as that of the prior art braces, generally being for treatment of curvature of the spine usually encountered in children and teenagers. While any practical brace has to provide the appropriate forces and pressures, other factors are also important in brace design so that the patient will be content to wear the device. Maximum comfort to an active wearer and minimum adverse affect on the physical appearance of the wearer are significant factors. Also adjustability while maintaining position during relatively rapid growth during this period of the patient's life are highly desirable.

We claim:

1. In an orthopedic brace, the combination of:
 a stiff anterior panel;
 right and left spaced stiff posterior panels;
 right and left elongated substantially rigid iliac crest members, with said right member fixed to said anterior and right panels and with said left member fixed to said anterior and left panels, with said crest members shaped such that they fit around the torso and over the iliac crest of a person when the brace is worn;
 adjustable strap means interconnecting said right and left panels; and
 a flexible pelvic band carried adjacent the lower ends of said panels below said crest members and extending from said right posterior panel to said anterior panel to said left posterior panel and fitting around the pelvis of a person when the brace is worn;
 with said stiff anterior and posterior panels, strap means and substantially rigid crest members providing a pre-determined distance between said anterior panel and said posterior panels and between a persons abdomen and back when the brace is worn.

2. An orthopedic brace as defined in claim 1 wherein said pelvic band is of one piece and fixed to each of said panels.

3. An orthopedic brace as defined in claim 1 including a flexible thoracic sling affixed to said anterior and one of said posterior panels above said crest member.

4. An orthopedic brace as defined in claim 1 including a substantially rigid bar carried on said anterior panel and projecting vertically upward therefrom.

5. An orthopedic brace as defined in claim 4 including a pad, and means for positioning said pad on said bar at a selected position.

6. An orthopedic brace as defined in claim 4 including a chest band affixed at each end to said right and left posterior panels respectively adjacent the upper ends thereof, and affixed at a central location to said bar.

7. An orthopedic brace as defined in claim 4 including substantially rigid right and left bars carried on said right and left posterior panels, respectively, and projecting vertically upward therefrom,
 ring means mounted at the upper end of said three bars forming a head enclosing structure, and
 pads carried on the inner portions of said structure for engaging the wearer.

8. An orthopedic brace as defined in claim 1 with said anterior panel extending upward overlying a persons ribs when the brace is worn and with said posterior panels extending upward overlying a persons scapulae when the brace is worn.

* * * * *